United States Patent
Stinson

(10) Patent No.: US 9,700,500 B1
(45) Date of Patent: Jul. 11, 2017

(54) DISPOSABLE WIPES COMPRISING OF WARMING LUBRICANTS, VITAMIN E OIL, AND ESSENTIAL OILS

(71) Applicant: Minnie Stinson, Homewood, IL (US)

(72) Inventor: Minnie Stinson, Homewood, IL (US)

(*) Notice: Subject to any disclaimer, the term of this patent is extended or adjusted under 35 U.S.C. 154(b) by 0 days.

(21) Appl. No.: 14/993,119

(22) Filed: Jan. 12, 2016

(51) Int. Cl.
| | | |
|---|---|---|
| *A61K 36/81* | (2006.01) | |
| *A61K 36/752* | (2006.01) | |
| *A61K 36/53* | (2006.01) | |
| *A61K 8/42* | (2006.01) | |
| *A61K 8/97* | (2017.01) | |
| *A61K 8/02* | (2006.01) | |
| *A61K 8/49* | (2006.01) | |
| *A61K 8/37* | (2006.01) | |
| *A61K 8/34* | (2006.01) | |
| *A61Q 19/10* | (2006.01) | |
| *A61Q 19/00* | (2006.01) | |

(52) U.S. Cl.
CPC ............. *A61K 8/42* (2013.01); *A61K 8/0208* (2013.01); *A61K 8/345* (2013.01); *A61K 8/37* (2013.01); *A61K 8/498* (2013.01); *A61K 8/97* (2013.01); *A61Q 19/007* (2013.01); *A61Q 19/10* (2013.01); *A61K 2800/596* (2013.01); *A61K 2800/74* (2013.01)

(58) Field of Classification Search
CPC ....... A61K 36/53; A61K 36/752; A61K 36/81
USPC .................................................. 424/736, 760
See application file for complete search history.

(56) References Cited

U.S. PATENT DOCUMENTS

2003/0143263 A1* 7/2003 Durden .................. A47L 13/17
424/443

\* cited by examiner

*Primary Examiner* — Chris R Tate
*Assistant Examiner* — Deborah Davis

(57) ABSTRACT

Disposable wipes comprising of warming lubricants, glycerol and capsaicin, vitamin E oil, essential oils, Lavender and Lemon, and propyl paraben. The fragrance free disposable wipes comprises of 85% purified water, 0.4.% glycerol, 0.1% capsaicin, 0.9% vitamin E oil, and 0.1% propyl paraben. The disposable wipes with fragrance comprises of 80% purified water, 0.4.% glycerol, 0.1% capsaicin, 0.9% vitamin E oil, 0.5% of either the essential oils, Lavender or Lemon, and 0.1% propyl paraben. The warming effect is achieved by having one or more additives in the lubricant which are either always active or activated by your body.

1 Claim, No Drawings

DISPOSABLE WIPES COMPRISING OF WARMING LUBRICANTS, VITAMIN E OIL, AND ESSENTIAL OILS

FIELD OF THE INVENTION

This invention relates to disposable wipes which when applied to the skin will have warming effects.

BACKGROUND OF THE INVENTION

Disposable wipes with warming lubricants, vitamin E oil, and essential oils. The disposable wipes can be used by everyone from an infant to an adult, and for those individuals that may have sensitive skin. Instead of having to wipe and/or wash with a cold wipe, you can do so with a nicely warm one.

Essential oils are used extensively in aromatherapy and various traditional medicinal systems. Due to the numerous health benefits of essential oils, they are increasingly being explored by the scientific community for the treatment of a variety of diseases including cancer, HIV, asthma, bronchitis, heart strokes, and many more.

Lavender oil comes from lavender (*Lavandula angustifolia*), an easy-to-grow, evergreen shrub that produces clumps of beautiful, scented flowers above green or silvery-gray foliage. The plant is native to northern Africa and the mountainous Mediterranean regions, and thrives best in sunny, stony habitats. Lavender is one of the most popular essential oils on the market because it smells great and is an effective stress-relieving oil. Lavender oil is known for its calming and relaxing properties Lemon oil is widely appreciated for its clean smell and has numerous therapeutic qualities as well. Lemon oil is uplifting and cleansing.

Propyl paraben may also be called propyl paraben. This is naturally derived from plants, as well as a few different types of insects. It is also manufactured synthetically for many industries such as the personal skin care and cosmetic industries. In personal skin care, Propyl paraben is a main ingredient in skin creams, lotions and moisturizing lotions and creams.

Vitamin E is an antioxidant and has various health benefits. This oil is extremely beneficial for proper nourishment and development of healthy skin and hair. It is no wonder that all the top manufacturers of skin care products use this oil as one of their main ingredients. Vitamin E oil, being a great moisturizer, is suitable for application on even the sensitive areas around the eyes.

Many warming lubricants contain glycerol, a sugar based compound that is colorless, odorless, and is an excellent base for the compounds used to create the warming sensation. Warming lubricants can be water-based or honey-based. Glycerol has three hydroxyl groups that are responsible for its solubility in water and its hygroscopic nature. The glycerol backbone is central to all lipids known as triglycerides. Glycerol can be either synthetic, or derived from plants, usually soybeans or palm, or animals, usually tallow. It can also be a blend of both animal and vegetable oils. Glycerol is used in medical and pharmaceutical and personal care preparations, mainly as a means of improving smoothness, providing lubrication and as a humectant.

Capsaicin also known as *Capsicum* is a commonly used ingredient in warming lubricants to achieve the warming effect. It is a major component in the chili pepper and can have a very strong warming effect.

These products are not intended to diagnose, treat, cure or prevent any disease.

DETAILED DESCRIPTION OF THE INVENTION

Disposable wipes comprising of warming lubricants, glycerol and/or capsaicin, vitamin E oil, and essential oils. The disposable wipes are fragrance and fragrance free. The disposable wipes with fragrance will comprise of purified water, the essential oils, Lavender and/or Lemon, glycerol and/or capsaicin, and vitamin E oil. The fragrance free disposable wipes will not contain the essential oils, Lavender or Lemon, and will comprise of purified water, warming lubricants, glycerol and/or capsaicin. The disposable wipes can be used by everyone from an infant to an adult, and for those individuals that may have sensitive skin.

Thermoception or thermoreception is the sense by which temperature is perceived. The warming thermoception is achieved on the contact with skin or by natural body moisture. The warming effect is achieved by having one or more additives in the lubricant which are either always active or activated by your body. Many warming lubricants contain glycerol, a sugar based compound that is colorless, odorless, and is an excellent base for the compounds used to create the warming sensation.

Capsaicin also known as *Capsicum* is a commonly used ingredient in warming lubricants to also achieve the warming effect. Capsaicin is a chemical compound that creates a warming sensation when applied topically.

Vitamin E is also known as alpha-tocopherol. Vitamin E oil is a supplement which contains vitamin E as its primary component. Therefore, this oil encompasses all the goodness of vitamin E in it. On account of it being natural and mild, the benefits of this oil can be enjoyed by practically anyone. Regular application of vitamin E oil on the skin improves the texture of the skin and helps to get rid of various skin problems.

Essential oils come with therapeutic benefits. Lavender is a stress reliever. Lemon oil is a multifaceted essential oil, and is a quick mood enhancer.

The fragrance free disposable wipes comprises of 85% purified water, 0.4% glycerol, 0.1% capsaicin, 0.9% vitamin E oil, and 0.1% propyl paraben.

The disposable wipes with fragrance comprises of 80% purified water, 0.4% glycerol, 0.1% capsaicin, 0.9% vitamin E oil, 0.5% of either of the essential oils, Lavender or Lemon, and 0.1% propyl paraben.

Propyl paraben may also be called propyl paraben. Propyl paraben is an ester of p-hydroxybenzoic acid. It is naturally derived from plants, as well as a few different types of insects. Propyl paraben is considered an indispensable ingredient in many personal skin care products because of its ability to improve the shelf life and the quality of skin care and hair care products. The use of Propyl paraben in cosmetics and personal skin care products is important to make products last their full shelf life. It preserves water-based solutions making it last for a longer shelf-life.

What is claimed:
1. A fragrant disposable wipe consisting essentially of:
85% purified water;
0.4% glycerol;
0.1% capsaicin;
0.9% vitamin E oil;
0.5% lavender essential oil and/or lemon essential oil; and
0.1% propyl paraben.

* * * * *